United States Patent [19]
Guinn et al.

[11] Patent Number: 5,877,032
[45] Date of Patent: Mar. 2, 1999

[54] PROCESS FOR DEVICE FABRICATION IN WHICH THE PLASMA ETCH IS CONTROLLED BY MONITORING OPTICAL EMISSION

[75] Inventors: Keith V. Guinn, Basking Ridge; Susan Clardy McNevin, New Providence, both of N.J.

[73] Assignee: Lucent Technologies Inc., Murray Hill, N.J.

[21] Appl. No.: 703,756

[22] Filed: Aug. 27, 1996

Related U.S. Application Data

[60] Provisional application No. 60/005,141, Oct. 12, 1995.
[51] Int. Cl.$^6$ ........................................... C23K 1/14
[52] U.S. Cl. ..................................... 438/9; 438/16; 216/60
[58] Field of Search .................. 216/60; 438/8, 438/9, 16

[56] References Cited

U.S. PATENT DOCUMENTS

| | | | |
|---|---|---|---|
| 4,289,188 | 9/1981 | Mizutani et al. | 216/60 |
| 4,457,820 | 7/1984 | Bergeron et al. | 438/9 |
| 4,528,438 | 7/1985 | Poulsen et al. | 219/121 PE |
| 4,609,426 | 9/1986 | Ogawa et al. | 156/626 |
| 4,676,868 | 6/1987 | Riley et al. | 156/643 |
| 4,857,136 | 8/1989 | Zajac | 438/16 |
| 5,308,414 | 5/1994 | O'Neill et al. | 156/626 |
| 5,322,590 | 6/1994 | Koshimizu | 156/626 |
| 5,348,614 | 9/1994 | Jerbic | 156/626 |
| 5,374,327 | 12/1994 | Imahashi et al. | 438/9 |
| 5,405,488 | 4/1995 | Dimitrelis et al. | 216/60 |
| 5,494,697 | 2/1996 | Blayo | 427/10 |
| 5,500,076 | 3/1996 | Jerbic | 438/9 |

FOREIGN PATENT DOCUMENTS

WO 95/08186  6/1994  Japan ........................... H01L 21/306

OTHER PUBLICATIONS

Guinn et al, J. Vac. Sci. Tech. A "Optical Emission Diagnostices for Contact Etching in Applied Materials", May 1996.

Harshbarger et al, J. Electronic Mat. "Optical Detector to Monitor Plasma Etching" pp. 429–440, May 1978.

*Primary Examiner*—Deborah Jones
*Attorney, Agent, or Firm*—Richard J. Botos; Patricia A. Verlangieri

[57] ABSTRACT

The present invention is directed to a process for device fabrication in which a pattern is transferred from a photoresist mask into an underlying layer of silicon dioxide. A plasma containing a fluorocarbon gas is used to etch the pattern into the underlying silicon dioxide layer. The plasma is monitored using optical emission spectroscopy to effect control of the etch process. The optical emission is monitored at select wavelengths. To control the process based on an observation of photoresist etch rate, two wavelengths are monitored. One is associated with a species that is produced by the interaction between the photoresist and the plasma, and one is associated with a species related to the plasma intensity. The ratio of the optical intensity at these two wavelengths is determined in real time during processing, and the ratio is associated with acceptable process conditions by referring to a predetermined calibration curve that associates a particular ratio with a particular photoresist etch rate for a given set of process conditions. If the ratio is observed to not be within a certain range of ratios determined to indicate acceptable process conditions, the plasma conditions are either changed to bring the ratio back within the desired range, or the process is stopped until the problem is corrected. To control the process based on an observation of contact hole etch rate, a wavelength associated with one species in the plasma is monitored at two different times during the etch. A ratio of the measured intensity at these two different times is obtained. Calibration information is then used to determine if the ratio indicates that the process is proceeding acceptably. If the ratio is not within the acceptable range, remedial action is taken.

12 Claims, 5 Drawing Sheets

PROCESS FOR DEVICE FABRICATION IN WHICH THE PLASMA ETCH IS CONTROLLED BY MONITORING OPTICAL EMISSION

CROSS-REFERENCE TO RELATED APPLICATION

This application claims priority of Provisional application Ser. No. 60/005,141 which was filed Oct. 12, 1995.

BACKGROUND OF THE INVENTION

1. Technical Field

The present invention is directed to a controlled plasma etch for use in semiconductor device fabrication.

2. Art Background

In processes for device fabrication, dry etching is a process frequently used as an expedient for the removal of materials from the surface of a semiconductor substrate. Dry etching is used either to selectively remove a certain portion of a layer of material on a substrate, thereby forming a patterned layer, or to transfer the pattern in a top layer into an underlying layer. Selective removal of materials from the substrate surface is an integral part of forming integrated circuit patterns on a semiconductor substrate. Plasma processes are commonly used to perform the dry etch step in integrated circuit device fabrication. The plasma is typically generated by exposing reactant gases to energy, which produces high energy species such as ions, neutral radicals, atoms, and molecules. When the plasma is applied to the surface of a semiconductor substrate, the high energy species remove materials therefrom.

In a plasma etch process, the portions of the substrate surface that are not desired to be removed by the etch are covered by a protective material typically referred to as a mask. The mask reveals only that portion of the substrate surface that is to be removed. However, it is not typically desirable to remove the material underlying the layer of material being removed. Therefore, it is desirable to accurately detect the end point of the plasma etch process.

One method for detecting the endpoint of a plasma etch process is to monitor the luminous intensity of the plasma. The endpoint is determined by observed changes in the luminous intensity of the plasma. In a process for the plasma etch of silicon dioxide using a fluorocarbon-based reactant gas, the luminous intensity of carbon monoxide, which is the reaction product of the high energy plasma species and the silicon dioxide, is monitored. A significant decrease in the luminous intensity of the carbon monoxide in the plasma indicates that the process is at or past endpoint.

As noted in U.S. Pat. No. 5,322,590 to Koshimizu, the problem with using an observed change in the luminous intensity of the etch reaction product is that, in current processes, the amount of surface etched is typically less than ten percent, and often less than one percent of the wafer surface. The remainder of the wafer surface is covered by the mask. Thus, the reaction products in the plasma are dominated by the reaction products from the interaction between the mask and the plasma. The change in the luminous intensity of the reaction products of the etch from before the etch endpoint to after endpoint is simply not readily observable because of the higher quantity of the many other species in the plasma and the fact that the emission spectra of the other species can interfere with the emission spectra of the monitored species in the plasma.

Koshimizu proposes monitoring an active etchant species, i.e., a radical in the plasma that actually reacts with the silicon dioxide, in the plasma and, from an observed change in the luminous intensity of the species, determine endpoint. Koshimizu proposes that the luminous intensity of the active etchant species should be noticeably lower when it is reacting with the silicon dioxide compared to after the silicon dioxide has been etched and the underlying material, typically silicon, is exposed. When the underlying silicon is exposed, the active etchant species is no longer consumed by reaction because the active etchant species does not react with silicon. Koshimizu propose enhancing this observation by ratioing the luminous intensity of the active etchant species with the reaction product on the theory that the combined changes in the luminous intensity of the product and reactant species will produce a more noticeable effect.

However, because the change in luminous intensity of a discrete species does not provide sufficient information to call endpoint in processes where the surface being etched is relatively small, i.e. ten percent or less, of the total substrate surface area, an alternative process for controlling the plasma process and for determining process endpoint, is desired.

SUMMARY OF THE INVENTION

The present invention is directed to a method for controlling a plasma etch process and specifically, a plasma etch process for removing silicon dioxide from the surface of a semiconductor wafer in semiconductor device fabrication. In the process, a semiconductor wafer covered with a layer of patterned photoresist is placed in a reaction chamber in which a plasma is generated. The pattern in the photoresist layer is throughout its thickness, such that a certain portion of the wafer is covered by the mask and another portion of the wafer is not covered. Silicon dioxide is formed on at least the unmasked portions of the wafer surface. A gas containing a fluorocarbon such as Freon®, a trademark of the Du Pont de Nemours Co., is introduced into the chamber. Sufficient energy is applied to the gas to generate a plasma. The silicon dioxide is etched by the plasma. The optical emission spectrum (OES) of the plasma is monitored as the etch proceeds and, based on discrete observations of the intensity of certain species in the plasma at predetermined wavelengths and comparing the intensity of those species to a predetermined calibration curve, the photoresist etch rate is determined. The etch rate of the contact holes in the silicon dioxide layer is also determined in this manner. Using the process of the present invention, the etch rate of contact holes with a diameter of less than 0.5 $\mu$m is determinable. The photoresist etch rate and/or the contact hole etch rate are observed to determine if the observed etch rate is within a predetermined range. If it is, the etch proceeds. If it is not, the etch is stopped or the process conditions are changed to bring the etch rate back within the predetermined range. Although the present invention is described in the context of a layer of photoresist overlying a layer of silicon dioxide, it is contemplated that the present invention is useful in monitoring the plasma etch of a wafer wherein there is a significant difference between the surface area of the photoresist mask and the surface area of the underlying layer exposed through the mask. For example, there is a significant difference when eighty percent or more of the wafer is masked by the photoresist and twenty percent or less of the oxide coated wafer underlying the mask is exposed through the mask.

In one embodiment, the photoresist-coated wafer is subjected to etching conditions using a $C_2F_6$ plasma. A $C_2F_6$ plasma is a conventional expedient used to etch silicon dioxide in processes for semiconductor device fabrication.

Mechanisms and conditions used to generate a $C_2F_6$ plasma are conventional and well known to one skilled in the art.

The OES obtained when etching a wafer with a photoresist mask overlying a silicon dioxide film with a fluorocarbon-containing plasma has peaks of luminous intensity at certain wavelengths. These peaks indicate the presence and relative concentration of certain species in the plasma. The OES is used to determine the etch rate of either the photoresist or the contact hole because the luminous intensity of certain species in the plasma is relatable to etch rate.

The species that is monitored and the manner in which it is monitored using OES is a function of the etch rate that is to be determined. If the OES is used to monitor the photoresist etch rate, the luminous intensity of at least two species in the OES must be monitored. One of the species is a byproduct of the interaction between the photoresist, carbon species on the wall of the etch tool, and the fluorocarbon plasma. It is advantageous if this species is $C_2$. The other monitored species is relatable to the plasma intensity. For example, the OES spectrum during the fluorocarbon etch of the photoresist masked wafer has a peak intensity at 440 nm that is associated with the species SiF in the plasma. As the intensity of the plasma increases, the intensity of this peak increases. As the intensity of the plasma decreases, the intensity of this peak decreases. Consequently, the peak associated with the SiF species is relatable to plasma intensity. Other species such as Si or F might also be monitored because the peaks in an OES spectrum associated with these species are also relatable to plasma intensity. Although the OES contains several peaks associated with the $C_2$ in the plasma, it is advantageous if the peak at 515 nm is monitored. It is advantageous if the peak at 440 nm in the OES is observed to monitor the presence of the SiF species in the plasma. If the presence of the Si species in the plasma is monitored, the optical emission at 288 nm is used. If the presence of the F species in the plasma is monitored, the optical emission at 703 nm is used. For convenience, the process is discussed in terms of the embodiment in which the optical emission of $C_2$ (at 515 nm) and SiF (at 440 nm) is observed.

The optical emission of these two species in the plasma is associated with the photoresist etch rate by measuring the thickness of the photoresist on a wafer before etching begins. The wafer is then plasma etched and the optical emission of the plasma at the relevant wavelengths is observed as a function of time. After etching is terminated, the thickness of the remaining photoresist is measured and the etch rate for the particular set of process conditions is determined.

If the OES is used to monitor contact hole etch rate, the optical emission associated with one species in the plasma is monitored. That species is any species in the plasma which can be associated with the contact hole etch rate. It is advantageous if the emission associated with the $C_2$ or SiF species in the plasma is monitored, because the signal-to-noise ratio of these signals is sufficiently high during the entire etch. The optical emission is associated with contact hole etch rate by measuring the SEM (scanning electron microscope) cross section of a number of patterned wafers after a timed etch. After the timed etch, the wafers have contact holes etched therein. The portion of the photoresist mask that remains after the timed etch is not stripped from the wafer prior to the SEM. From the SEM, the depth of the contact holes is measured. The etch rate is then calculated from the depth of the contact holes and the duration of the etch. The etch rate is then associated with the OES trace that was obtained during the etch.

It is advantageous if the above-described process of associating etch rate with OES parameters is repeated a number of times, wherein a discrete processing parameter (e.g., temperature, flow rate, pressure, rf bias, source power, $O_2$ clean time) is varied to change the etch rate of the photoresist and/or the contact hole, and, in turn, determine the correlation between the optical emission trace and the photoresist and/or contact hole etch rate. The parameters selected for variation, and the amount by which the parameters are varied, are selected to obtain traces over a range of etch rates. Therefore, only parameters that effect the etch rate when varied are selected for this purpose. It is advantageous if the parameters selected for variation provide etch rates that vary by more than a range of a factor of two or three from each other.

For example, the effect of a change in the plasma source power on the photoresist etch rate is observed by etching several wafers under identical process conditions except that the plasma source power is varied from etch to etch. Traces of the intensity at the relevant wavelengths in the OES over time are obtained, and these traces are associated with the photoresist etch rate. The process is then repeated for another discrete processing parameter such as temperature of the chamber.

In another embodiment of the present invention, the effect of a change in the duration of the $O_2$ clean of the chamber (the etch chamber is cleaned with $O_2$ between etches to remove deposits that collect on the wall of the chamber during an etch) on the contact hole etch rate is observed. There is a complex association between the duration of the $O_2$ clean and the contact hole etch rate. If the duration of the $O_2$ clean is insufficient to result in the removal of all deposits from the chamber, the contact hole etch rate will vary from etch to etch. Because such an effect is cumulative, the effect is more pronounced with each etch. The relationship between the duration of the $O_2$ clean and the etch rate is measured as a function of the number of wafers etched. An OES trace is obtained at the selected wavelength over time for each etch, and the trace is associated with etch rate in the above-described manner.

After the traces are obtained for the various etch rates as described above, a ratio of the signals from each trace are correlated to the particular etch rate. This can be done in a number of different ways. In one embodiment, the ratio of the intensity of two signals associated with two different species in the plasma, e.g. $C_2$ and SiF, at a discrete point in time during the etch, e.g., the ratio at 75 seconds into the etch, is obtained for each trace. This ratio is then mapped as a function of the photoresist etch rate. This information is then used to monitor etch rate by observing the ratio in real time during an etch and referring to the correlation of the ratio to the etch rate to determine the etch rate.

In another embodiment, the intensity of a signal associated with a single species in the plasma, e.g. $C_2$, SiF, etc., is monitored and the ratio of this intensity at two different times (i.e. $t_1$ and $t_2$) during the etch is obtained. This ratio is then mapped as a function of contact hole etch rate. The etch rate is then determinable in real time by obtaining a ratio of the intensity of a corresponding signal at times $t_1$ and $t_2$ from an OES trace and, from the calibration information previously obtained, finding an etch rate that is associated with this ratio.

In a third embodiment an integrated value of the ratio of the intensity of a signal associated with a first species to the intensity of a signal associated with a second species is computed over the entire etch. This integrated value is associated with an etch rate in the above-described manner. In all of the above-described embodiments, after a particular ratio is correlated with a particular etch rate, the relationship between the ratio and the etch rate is determined by plotting the ratio as a function of etch rate. This plot is a calibration curve that is then used to control the process.

In one embodiment of the present invention, the signal to noise ratio of the $C_2$-associated signal in the OES is reduced by etching a silicon wafer without photoresist or silicon dioxide thereon in the RF-generated fluorocarbon plasma. The $C_2$ signal in the OES is observed. The $C_2$ signal contains contributions from the fluorocarbon gas and from residual carbon containing species on the interior of the chamber. Therefore, by obtaining the $C_2$ signal in a plasma with a blank silicon wafer therein and a ratio of that signal to the $C_2$ signal obtained when etching a photoresist-covered wafer, the background effects of the fluorocarbon gas and chamber interior in the $C_2$ signal of an OES (obtained under the same etch conditions as the etch conditions used to obtain the background signal) can be removed.

Once the calibration curve is obtained as described above, the OES obtained during etching is used to effect real time process control. For example, the ratio of the $C_2$ peak at 515 nm to the SiF peak at 440 nm is determined from the OES at time t, and this ratio is used to determine the photoresist etch rate using the calibration curve obtained as previously described. Once the etch rate is determined, that information is used to control the process. If the etch rate of the photoresist at time t is "out of specification," i.e. it is higher or lower than a predetermined value, thereby indicating a problem with the process, the process can be halted and the problem corrected without adverse processing consequences to several, perhaps many, wafers before the problem is even detected. For example, knowing the etch rate at time t, the operator can, if necessary, adjust the etch conditions, e.g. pressure, flow rate, composition of the reactant gas, etc., as required to bring the etch rate back to within the desired range.

Although the embodiments of the invention described herein are discussed in terms of photoresist etch rate and contact hole etch rate, an actual determination of the etch rate is not critical to the process. Rather, the etch rate can be correlated to the ratio of the $C_2$ and SiF signals in the plasma. Once an acceptable range of ratios for a particular process is determined using the calibration method described above, the ratios can be monitored to control the process in real time. This provides advantages especially in pattern transfer processes wherein the surface area of the overlying layer is large compared to the unmasked portion of the underlying layer, or vice-versa. For example, the process of the present invention can be used to monitor the etch of contact holes or vias in the silicon dioxide layer underlying the mask. By controlling the plasma conditions to maintain the ratio of $C_2$ to SiF within the desired range, overetch or underetch of the silicon dioxide underlying the mask can be avoided. Thus, by monitoring the $C_2$ and SiF species periodically or continually during the etch, the etch process is controllable in real time.

DETAILED DESCRIPTION

The present invention is directed to a process for device fabrication in which contact holes are etched into silicon dioxide. In the context of this process, a patterned photoresist mask is formed over a silicon wafer with a layer of oxide thereon. It is advantageous if the photoresist is patterned in such a way that less than fifty percent of the wafer surface is unmasked oxide and more than fifty percent of the wafer surface is covered by the photoresist mask. The process of the present invention utilizes OES to monitor the plasma used to transfer the holes in the photoresist pattern into the underlying oxide.

Typically a fluorocarbon-containing plasma is used to transfer the holes into the underlying oxide. The OES of this plasma environment is monitored to provide real time process control of the plasma etch process. The method and apparatus for generating the fluorocarbon-containing plasma are conventional, well-known to one skilled in the art, and not detailed herein. One example of a suitable apparatus for performing such an etch with a fluorocarbon plasma is the 5300 HDP etcher from Applied Materials of Sunnyvale, California (also known as Omega). The apparatus is operated at pressures typically less than about 75 mTorr and with an electron density in excess of about $10^{11}/cm^3$.

The OES of the plasma is monitored using conventional apparatus which separates the light from the plasma into component wavelengths that measure the light intensity. One example of an OES system has a CCD array detector (model LS2000C from Alton Instruments of Garden Grove, Calif.) coupled to a spectrograph (Model CP140 from Instruments SA of Edison, N.J.). This particular system is sensitive to emissions in the range of about 200 nm to about 850 nm, has a resolution of less than 2 nm, and scan times of less than 0.1 seconds.

The OES is monitored over time at one or more selected wavelengths as the plasma is used to etch the wafer. In order to practice the process of the present invention, a relationship between the photoresist etch rate and/or the contact hole etch rate and the intensity of the signals in the OES at the selected wavelengths must be determined. To determine the photoresist etch rate, the photoresist thickness is measured before and after each timed etch. The photoresist etch rate is determined by dividing the change in thickness by the etch time. The contact hole etch rate is determined by measuring the depth of contact holes after a timed etch. An SEM is used to measure the depth of the contact hole. The contact hole etch rate is determined by dividing the depth of the contact hole by the duration of the etch.

Figure 1:
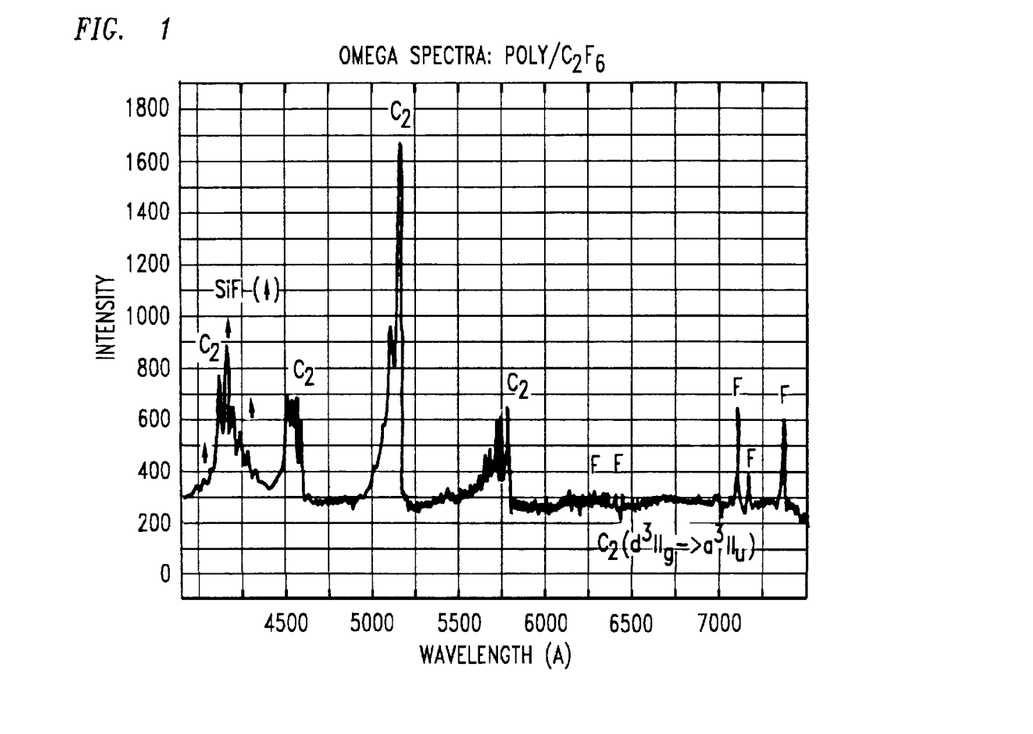
FIG. 1 is an OES spectrum of a $C_2F_6$ plasma used to etch a wafer with a photoresist mask overlying a layer of silicon dioxide.

The relationship between the etch rate and the OES signals is determined in a number of different ways. In one embodiment which is particularly suited for monitoring the photoresist etch rate during the plasma etch, wavelengths associated with at least two different species in the plasma are monitored over time during the etch. One of the wavelengths monitored is associated with a peak intensity of a species associated with the interaction between the plasma and the photoresist and one of the species is associated with the plasma intensity. Examples of suitable species pairs are $C_2$ and SiF, $C_2$ and Si, and $C_2$ and F. Some of these species are associated with peaks at several different wavelengths in an OES spectrum of a fluorocarbon plasma. For example, as shown in FIG. 1, an OES spectrum of a $C_2F_6$ plasma used to etch a wafer masked as described above has intensity peaks at several different wavelengths that are associated with $C_2$. The spectra was obtained using the apparatus specified above. To practice the process of the present invention, only one wavelength associated with one of each of the species in one of the above-described species pairs need be monitored. In one embodiment, the OES signal at 440 nm (associated with SiF species) and at 515 nm (associated with the $C_2$ species) are monitored.

The intensity of the $C_2$ and SiF signals at their respective selected wavelengths is monitored as a function of time during the etch. A ratio of the $C_2$ and SiF signals is then determined, either by selecting a ratio of the two signals at a distinct point in time during the etch, or by integrating the value of each signal over time and obtaining a ratio of the integrated signals. This ratio is then associated with the etch rate for that wafer, which is determined as previously described.

This process is repeated for etches at a variety of etch rates. In the embodiment of the present invention in which a calibration curve for the photoresist etch rate is obtained, the etch rate is varied by altering a discrete process parameter such as plasma source power or chamber "roof" temperature. In one example, the etch rate varies in the range of about 900 Å/min to about 3400 Å/min by varying the source power and the roof temperature of the etch. This is accomplished by performing a series of etches at four different source powers: 2350 Watts, 2500 Watts, 2650 Watts, and 2800 Watts. Three etches are performed at each source power: one at a roof temperature of about 240° C., one at a temperature of about 250° C., and one at about 260° C. Other etch parameters such as the bias and the pressure remain constant as the parameters described above are varied. A calibration curve is thereby obtained that associates a particular ratio of the $C_2$ and SiF signals with a particular photoresist etch rate.

In the embodiment of the present invention in which calibration curve is obtained to monitor the contact hole etch rate, the duration of the $O_2$ chamber clean between etches is selected so that the contact hole etch rate varies from wafer to wafer. The other etch parameters remain constant from wafer to wafer. An $O_2$ chamber clean of 40 seconds or less ensures that the chamber will not be completely cleaned between wafers, and that the etch rate will vary from wafer to wafer as a result of the build up of residues in the chamber. A duration of about 40 seconds is advantageous because the contact etch rate varies from wafer to wafer under these conditions but the photoresist etch rate does not. A cassette loaded with wafers (e.g. 25) is then etched with the prescribed duration of $O_2$ chamber clean between the each etch. An OES trace is obtained for each wafer in the sequence. The intensity of a signal associated with a species in the plasma (e.g. $C_2$ or SiF) was measured at two different times ($t_1$ and $t_2$) during the etch and a ratio of these two intensities is associated with the etch rate in the manner previously described.

Although the parameters varied to obtain the calibration curve and the amount by which each parameter is varied is largely a matter of design choice, it is advantageous if the etch rate is varied by about +/−50 percent of the target etch rate. It is advantageous if the ratio of the $C_2$ signal to the SiF signal is obtained from an OES of a blank wafer exposed to the same etch conditions. The "photoresist wafer ratio" is divided by the "blank wafer ratio" to obtain a ratio with from which background effects are removed, and the photoresist etch rate is obtained from this ratio.

Once the calibration curve is obtained, the OES spectrum is obtained for real time process control of the plasma etch process by monitoring the signal intensity of the spectrum at the selected wavelengths during the etch process, and calculating the etch rate based upon the ratio of the two signals. A real time determination of the photoresist etch rate enables better process control, because, if the photoresist is observed to be outside of a predetermined range, process conditions can be adjusted in real time or before etching subsequent wafers to bring the photoresist etch rate back to within the desired range.

The calibration curve, once generated, is used to control processes that are similar to the process conditions used to generate the calibration curve. Changes in process conditions that will require the generation of a new calibration curve will be apparent to one skilled in the art. For example, although the process conditions can be varied throughout the range of conditions that were varied to obtain the calibration curve (e.g., the source power and temperature varied above), a change in other process conditions could necessitate the generation of a new calibration curve. For example, if the preheat conditions of the etcher are changed, a new calibration curve may be required. For example, if the preheat time used to generate a calibration curve is 5 seconds, a new calibration curve is required if the preheat time is changed to 30 seconds, but not if the preheat time is changed to 10 seconds. If the composition of the etchant is changed from the composition used in the etches monitored to obtain the calibration curve, then a new calibration curve would have to be obtained for the new etchant. If the amount of the wafer covered by the photoresist is changed by more than about +/−10 percent from the amount for the wafers etched to obtain the calibration curve, a new calibration curve is required. Similarly, significant changes in rf power, pressure, etchant gas flow rate, etc. from the etch conditions used to generate the calibration curve can require the generation of a new calibration curve.

EXAMPLE 1

The wafers etched to obtain the calibration curve for monitoring the photoresist etch rate during a plasma etch were silicon wafers that were 100 percent covered with an 8000 Å-thick layer of an I-line photoresist, Shipley 1800, that was obtained from Shipley of Marlboro, Mass. The wafers etched to obtain the calibration curve for monitoring the contact hole etch rate during a plasma etch were silicon wafers with a 1.02 $\mu$m thick layer of oxide formed thereon. The surface of these wafers had a layer of ARCH II® deep UV (ultraviolet) resist coated over 98 percent of the wafer surface. The ARCH II® photoresist is manufactured by the OCG Corp.

The wafers were etched in an Applied Materials Model 5300 HDP (Omega) oxide etcher. The chamber pressure was 4 mTorr and the electron density in the plasma was between about $10^{11}$ to $10^{12}/cm^3$. The etch apparatus was equipped with an RF source coil to generate the plasma and an RF bias platen to control the ion bombardment energy. The quartz sidewall temperature was maintained at 220° C. The chamber was preheated, using the plasma source power and no bias power, for 5 seconds before the etch began. The flow rate of the $C_2F_6$ plasma was 25 sccm.

The calibration curve for monitoring photoresist etch rate was generated by varying the source power from 2350 W to 2800 W in the previously described increments of 600 W bias power. The etcher had a heated chamber with a silicon top plate and a quartz side wall. The temperature of the silicon top plate was varied from about 240° C. to about 260° C. in the previously described increments to obtain the calibration curve.

Figure 2:
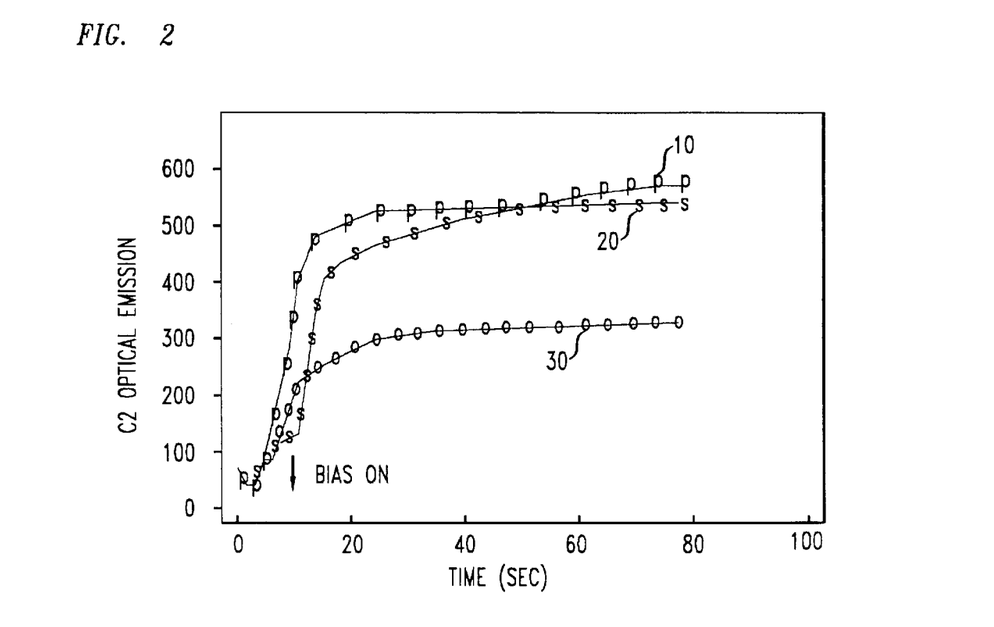
FIG. 2 illustrates a trace of the intensity of the $C_2$ emission at 515 nm over time during the plasma etch of a photoresist-coated wafer, an oxide-coated silicon wafer, and a bare silicon wafer.
Figure 3:
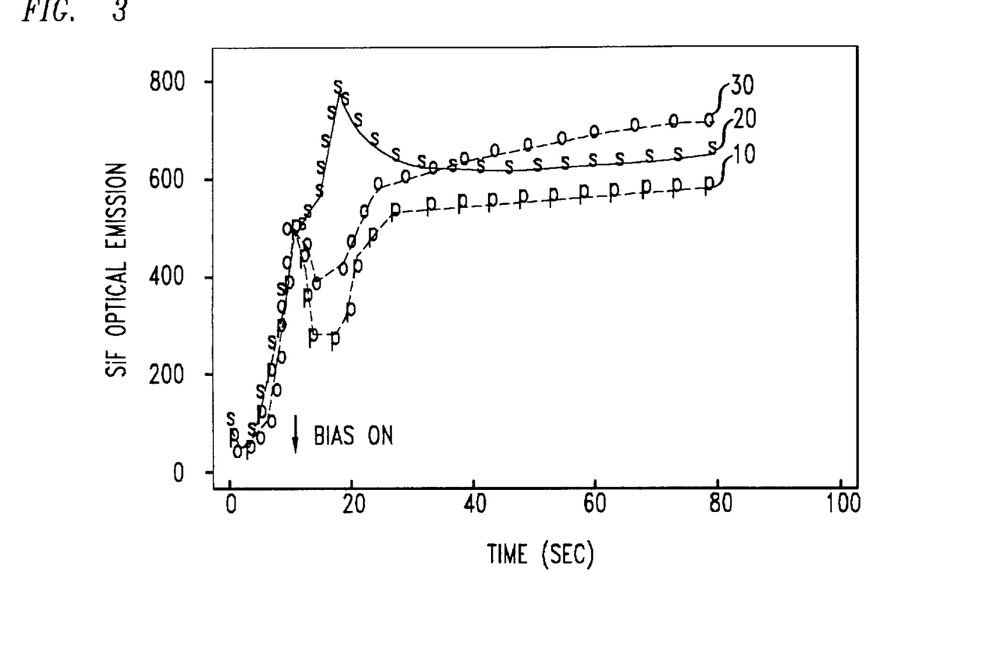
FIG. 3 illustrates a trace of the intensity of the SiF emission at 440 nm over time during the plasma etch of a photoresist-coated wafer, an oxide-coated silicon wafer, and a bare silicon wafer.

The optical emission of $C_2$ at the 515 nm wavelength is illustrated in FIG. 2, which shows the intensity of the $C_2$ peak as a function of time for three different types of wafers: a wafer with a surface 100 percent covered by photoresist 10; a bare silicon wafer 20; and a silicon wafer with a layer of oxide formed thereon 30. The data in FIG. 2 was obtained from an OES of a plasma generated with a source power of 2500 W and a roof temperature of 250° C. Under these conditions, the oxide etch rate was 7548 Å/min and the photoresist etch rate was 1965 Å/min. FIG. 3 shows the intensity of the SiF signal at the 440 nm wavelength for the same three wafers used to obtain the graph in FIG. 2 using the identical etch conditions.

Figure 4:
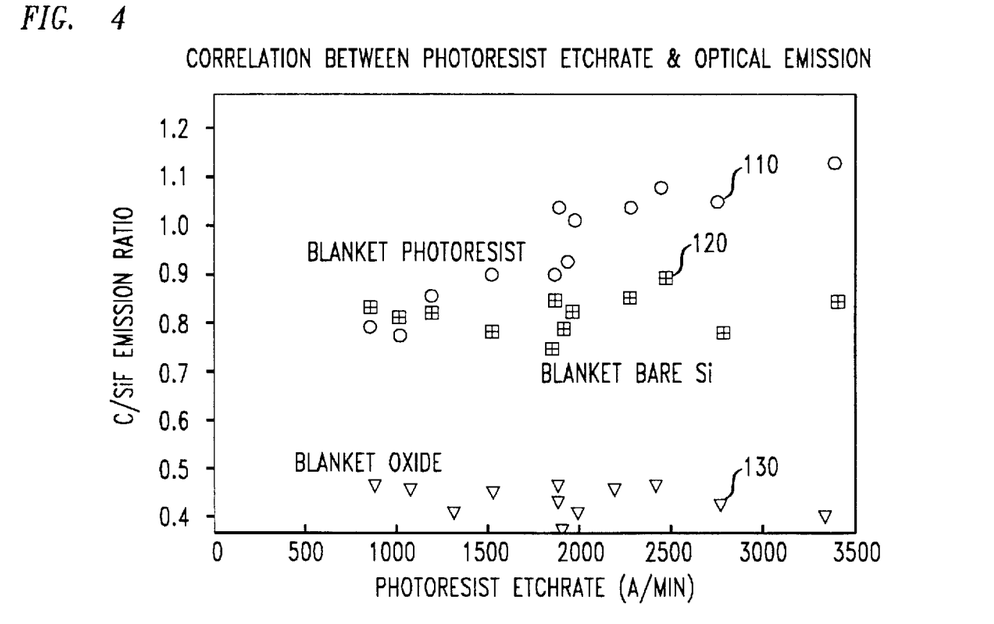
FIG. 4 illustrates the relationship between the $C_2$ and SiF emission ratio and the etch rate for the photoresist-coated, oxide coated, and bare silicon wafers.

For each discrete set of etch conditions (for each source power used at each temperature) a ratio of the $C_2$ signal to the SiF signal in the OES at the above specified wavelength was determined. This ratio was plotted as a function of photoresist etch rate. The photoresist etch rate was determined by measuring the film thickness before and after the etch, and determining the change in thickness as a function of time. The relationship between the $C_2$/SiF ratio and the photoresist etch rate is illustrated by the open circles 110, in FIG. 4. The $C_2$/SiF ratio was also determined for bare silicon wafers subjected to identical etch conditions. These ratios are indicated by the squares 120 in FIG. 4. The $C_2$/SiF ratio was also determined for oxide coated wafers subjected to identical conditions. These ratios are indicated by the triangles 130 in FIG. 4. A circle 110, square 120, and triangle 130 on the same vertical axis indicates a photoresist covered wafer, a bare silicon wafer, and an oxide coated wafer, respectively, which were subjected to the same identical set of etching conditions.

Figure 5:
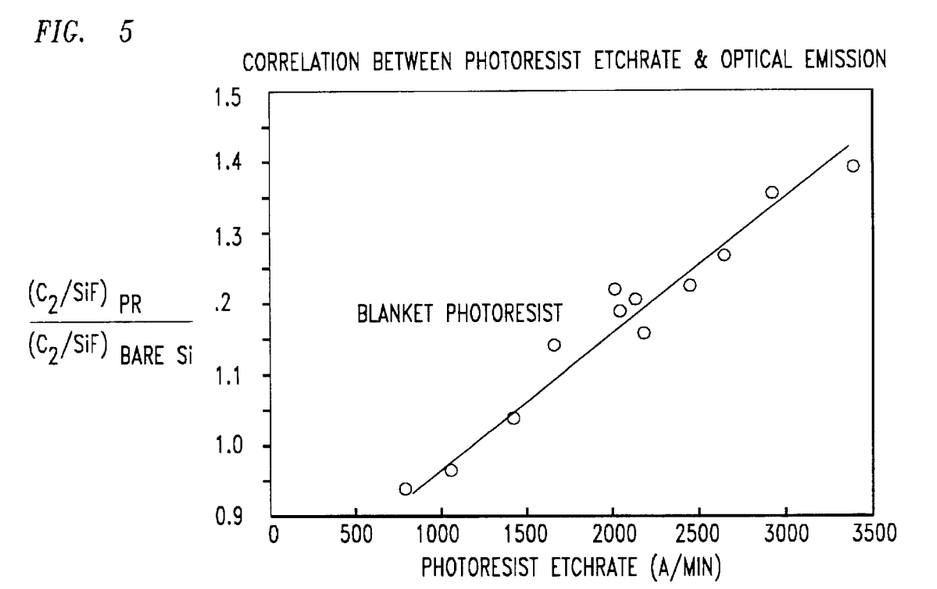
FIG. 5 illustrates the relationship between etch rate and the $C_2$ and SiF emission ratio for the photoresist-coated wafer divided by the same ratio for the bare silicon wafer.

A second ratio was then obtained to subtract some of the background noise from the $C_2$/SiF ratio. This second ratio was the $C_2$/SiF ratio obtained from the OES of the plasma used to etch the photoresist wafer divided by the $C_2$/SiF ratio obtained from the OES of the plasma in which a bare silicon wafer was placed under identical etching conditions. This ratio ($C_2$/SiF)photoresist/($C_2$/SiF)bare silicon is plotted is a function of photoresist etch rate. The resulting calibration curve is illustrated in FIG. 5.

Once the calibration curve is obtained as described above, it is used to monitor the etch process in the following manner. An OES of the plasma used to etch the pattern in the pattern in a photoresist into an underlying silicon dioxide layer is monitored. The intensity of the $C_2$ and SiF species at the appropriate wavelengths is observed, and a ratio of these two intensities is obtained. This ratio is then divided by a ratio of $C_2$ to SiF previously obtained for a blank silicon wafer obtained by subjecting the blank silicon wafer to the identical etch conditions. The ratio obtained is then used to determine the photoresist etch rate in real time by referencing the previously calibrated relationship between this ratio and the photoresist etch rate. If the photoresist etch rate is within some previously determined operating window (e.g. 1500 Å/min to 2500 Å/min) then the process is proceeding acceptably. If the etch rate so determined is outside the desired range, appropriate corrective action is taken in correct the problem. This corrective action includes adjusting the process conditions to bring the etch rate back within the window, or stopping the process until the problem is corrected.

Figure 6A:
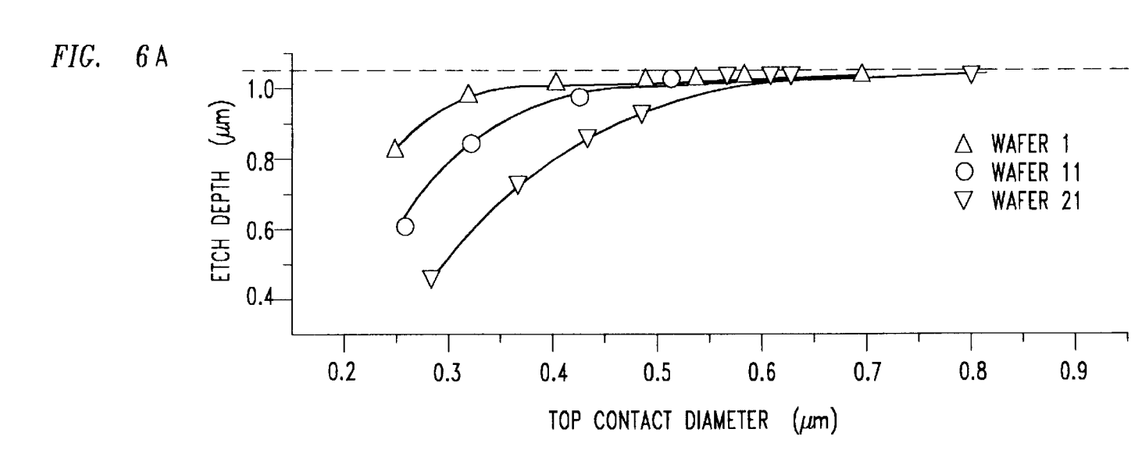
FIG. 6A illustrates the difference in the contact hole depth observed in a sequence of wafers when the duration of the $O_2$ clean between wafers is inadequate to completely clean the chamber.

The calibration curve for monitoring the contact hole etch rate was generated by sequentially etching 25 ARCH II®-coated wafer in a chamber. The duration of the $O_2$ chamber clean between etches was about 40 seconds. Because a 40 second clean was inadequate to remove all of the impurities in the chamber from the previous etch, the contact hole etch rate varied from wafer to wafer. The contact hole etch rate for each wafer was determined by timing each etch and measuring the depth of the resulting contact holes after the etch using an SEM microscope. As illustrated in FIG. 6A, the depth of the contact hole varied with the diameter of the contact hole and as a function of the place of the wafer in the wafer sequence. FIG. 6A illustrates the depth of contact holes in wafers 1, 11, and 21 in the 25-wafer sequence. FIG. 6A illustrates that, for contact holes with a diameter of 0.5 μm or less, the contact holes were progressively shallower for each wafer in the sequence. Since the duration of the etch was constant from wafer to wafer, FIG. 6A illustrates that the contact hole etch rate was progressively slower for each wafer in the wafer sequence.

Figure 6B:
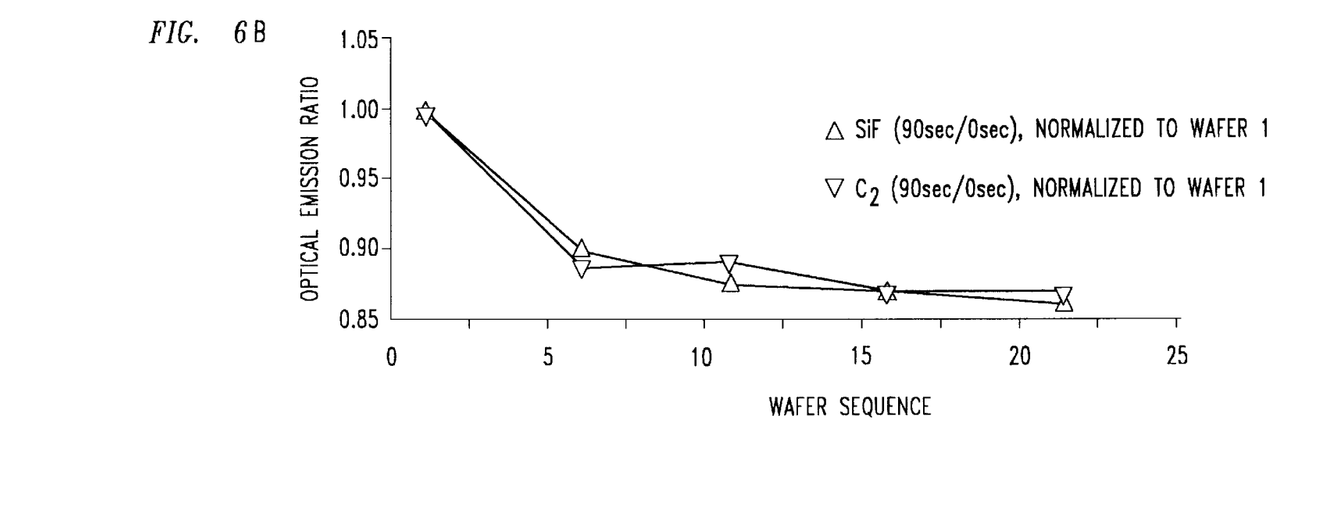
FIG. 6B illustrates the ratio of the intensity of signals ($C_2$ and SiF) at two different times during the etch and change in this ratio in a wafer sequence.

An OES trace was also obtained during each etch. In this example a trace was obtained at both the 515 nm wavelength (the signal associated with the $C_2$ species) and the 440 nm wavelength (the signal associated with the SiF species). However, only one signal is required to generate the calibration curve. The intensity of the signals at time $t_1$ (0 seconds) and time $t_2$ (90 seconds) were measured, and the ratio of these two signals for each trace was associated with the etch rate. As illustrated in FIG. 6B, this ratio varied from wafer to wafer in the 25-wafer sequence. Because the photoresist etch rate remained constant from wafer to wafer, the ratio of the $C_2$ signals and the ratio of the SiF signals had the same dependence on wafer sequence.

Figure 7:
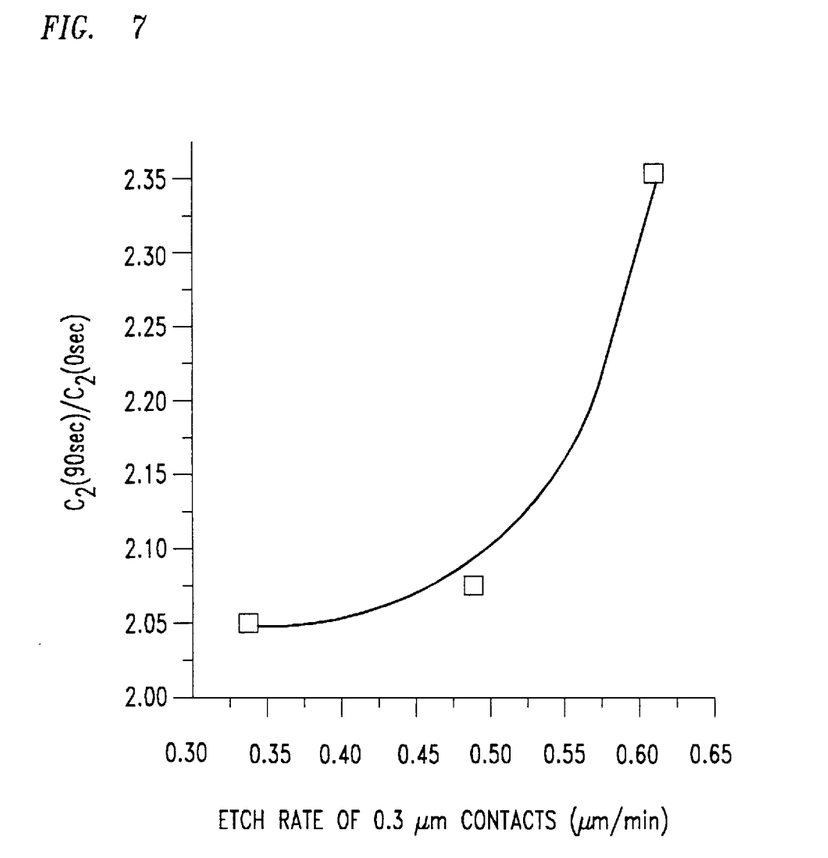
FIG. 7 illustrates a calibration curve generated from the data illustrated in FIGS. 6A and 6B that is used as a diagnostic to control the etch rate of the contact hole.

FIG. 7 illustrates a calibration curve generated from the information in FIGS. 6A and 6B. Specifically, the ratio of $C_2$ at 90 seconds to $C_2$ at 0 seconds is mapped as a function of etch rate.

This calibration curve is used to monitor the contact hole etch rate by monitoring the $C_2$-associated signal of the OES during a plasma etch. At 90 seconds into the etch the ratio of $C_2$ (90 sec.) to $C_2$ (0 sec.) is obtained. The contact hole etch rate is determined by using the calibration information to determine the etch rate based upon the ratio. If the etch rate is within the desired parameters, no adjustment to the process is required. If the etch rate is outside the desired parameters, the etch is either halted, or the etch conditions are adjusted to bring the etch rate back into specification.

The invention claimed is:

1. A process for device fabrication comprising:

placing a substrate in a reaction chamber which is adapted for plasma generation, the substrate having a layer of silicon dioxide on at least a portion of one surface thereof, and a photoresist mask over the silicon dioxide layer wherein at least a portion of the silicon dioxide layer is exposed through the mask;

introducing a fluorocarbon-containing gas in the reaction chamber;

generating a plasma in the reaction chamber to remove the silicon dioxide exposed through the mask from the substrate;

monitoring the optical emission of the plasma and measuring the luminous intensity associated with at least one species in the plasma;

calculating a value from the measured luminous intensity;

comparing the calculated value to a range of calibration values, wherein the range of calibration values is associated with either an etch rate of the photoresist mask or an etch rate of the silicon dioxide layer; and controlling the process based upon the comparison.

2. The process of claim 1 wherein the process is controlled by adjusting a process parameter if the calculated value is not within the range of calibration values.

3. The process of claim 2 wherein the luminous intensity of a first species and the luminous intensity of a second species in the plasma are monitored as a function of time, wherein the luminous intensity of the first species is associated with the interaction between the photoresist and the plasma and the luminous intensity of the second species is associated with plasma intensity, wherein the calculated value is the ratio of the luminous intensity associated with the first species to the luminous intensity associated with the second species.

4. The process of claim 3 wherein the first species is $C_2$ and the second species is selected from the groups consisting of SiF, Si, and F.

5. The process of claim 4 wherein the first species is $C_2$ monitored at 515 nm and the second species is SiF monitored at 440 nm.

6. The process of claim 3 wherein the range of calibration ratios associated with the etch rate are determined from a calibration curve that associates a particular ratio with a particular photoresist etch rate for a given set of process conditions.

7. The process of claim 6 further comprising adjusting the process conditions if the calculated ratio is not within the range of calibration ratios associated with the etch rate of the particular photoresist.

8. The process of claim 2 wherein the luminous intensity of the species in the plasma is monitored over time and wherein the calculated value is the ratio of the luminous intensity associated with the species at a time $t_1$ to the luminous intensity associated with the species at a time $t_2$, wherein both times $t_1$ and $t_2$ occur during the etch process.

9. The process of claim 8 wherein the etch rate is a contact hole etch rate.

10. The process of claim 9 wherein the species is selected from the groups consisting of $C_2$ and SiF.

11. The process of claim 10 wherein the range of calibration ratios is determined from a calibration curve that associates a particular ratio with a particular contact hole etch rate for a given set of process conditions.

12. The process of claim 11 further comprising adjusting the process conditions if the calculated ratio is not within the range of calibration ratios determined from the calibration curve that associates the particular ratio with the particular etch rate for the given set of process conditions.

* * * * *